(12) United States Patent
García García et al.

(10) Patent No.: US 12,196,546 B2
(45) Date of Patent: Jan. 14, 2025

(54) FRUIT-ON-TREE SIZING DEVICE

(71) Applicant: AGERPIX TECHNOLOGIES, S.L.U., Soria (ES)

(72) Inventors: Javier García García, Soria (ES); Antonio Cabezón Cascante, Soria (ES); David Francés Peñuelas, Soria (ES)

(73) Assignee: AGERPIX TECHNOLOGIES, S.L.U., Soria (ES)

( * ) Notice: Subject to any disclaimer, the term of this patent is extended or adjusted under 35 U.S.C. 154(b) by 440 days.

(21) Appl. No.: 17/768,131

(22) PCT Filed: Oct. 7, 2020

(86) PCT No.: PCT/ES2020/070606
§ 371 (c)(1),
(2) Date: Apr. 11, 2022

(87) PCT Pub. No.: WO2021/074467
PCT Pub. Date: Apr. 22, 2021

(65) Prior Publication Data
US 2023/0280144 A1    Sep. 7, 2023

(30) Foreign Application Priority Data

Oct. 17, 2019  (ES) .................................. 201930923

(51) Int. Cl.
*G01B 5/00* (2006.01)
*G01B 5/08* (2006.01)
(Continued)

(52) U.S. Cl.
CPC ............. *G01B 5/0035* (2013.01); *G01B 5/08* (2013.01); *G01B 21/10* (2013.01); *G01N 33/025* (2013.01); *G01B 2210/58* (2013.01)

(58) Field of Classification Search
CPC ........ G01B 5/08; G01B 5/0035; G01B 21/10; G01B 5/201; G01B 2210/58;
(Continued)

(56) References Cited

U.S. PATENT DOCUMENTS

| 887,092 A | * | 5/1908 | Hearson | ................... | B25D 5/02 33/675 |
| 2022/0282408 A1 | * | 9/2022 | Charleux | ................. | G01B 5/08 |

FOREIGN PATENT DOCUMENTS

CN     206601116 U  * 10/2017
DE     202004019186 U1    4/2005

OTHER PUBLICATIONS

Subir Das, "Continuous radial growth rate monitoring of horticultural crops using an optical mouse", Journal, 2019, 1-7, vol. 297, Sensors and Actuators A: Physical.
(Continued)

*Primary Examiner* — Yoshihisa Ishizuka
*Assistant Examiner* — Carter W Ferrell
(74) *Attorney, Agent, or Firm* — Hayes Soloway PC (57) ABSTRACT

A fruit-on-tree sizing device includes a lower annular disc and an upper annular disc, from which first flexible arms and second flexible arms, with curved configuration, start internally, in opposite directions, and which respectively form a lower opening and an upper opening wherein the fruit is positioned. As the diameter of the fruit increases, the first flexible arms and the second flexible arms force the upper annular disc and the lower annular disc to rotate on themselves, in opposite directions. The device further includes a reading module intended for quantifying the relative movement of the upper annular disc with respect to the lower annular disc, and transmitter which transmits the measurements obtained to an external device.

9 Claims, 7 Drawing Sheets

(51) Int. Cl.
*G01B 21/10* (2006.01)
*G01N 33/02* (2006.01)

(58) Field of Classification Search
CPC ........ G01B 33/025; G01B 21/02; G01B 5/02;
G01B 5/20; A01D 46/24
See application file for complete search history.

(56) References Cited

OTHER PUBLICATIONS

Phyto Sensor Group, "Phyto-Sensor System Fl-Lz, Fl-Sz Fruit Growth Sensors", Article, 2014, 1-6.

* cited by examiner

FRUIT-ON-TREE SIZING DEVICE

CROSS-REFERENCE TO RELATED APPLICATIONS AND PRIORITY

This patent application claims priority from PCT Application No. PCT/ES2020/070606 filed Oct. 7, 2020, which claims priority from Spanish Patent Application No. P201930923 filed Oct. 17, 2019. Each of these patent applications are herein incorporated by reference in their entirety.

OBJECT OF THE INVENTION

The object of the invention is a fruit sizing device that is placed around the fruit while it is on the tree, from when it has a very small diameter until it is picked. The device measures the data of the diameter or size of the fruit and sends it by radio frequency to an external device, enabling the updated data to be known at all times.

BACKGROUND OF THE INVENTION

At present, fruit is collected, selected, treated and classified according to its size, that is, according to the maximum diameter thereof. In most cases, this determination of the features is made once the fruit has been picked, which in many cases entails having to discard some because they have been picked too early, when they have not yet reached the appropriate size, or too late, when they have a larger size than desired.

Furthermore, it is of interest to know the development of the fruit in different trees at all times, in order to make decisions regarding the management of the trees, in terms of irrigation, fertilisation, etc.

To try to solve the two previous points, a series of sizing devices have been developed over time which are placed directly on the fruit, usually surrounding it, when it is still on the tree, and from when it is very small, thus enabling the development of the fruit to be known via the size thereof. However, these devices have a number of disadvantages that are described below.

First of all, these devices, which are placed clasping the fruit by the larger diameter thereof, damage the outer skin, which is extremely delicate. Furthermore, they exert high pressure that can affect fruit growth, deforming it.

Moreover, they are devices of high weight, so that on many occasions the fruit falls to the ground, the fruit being no longer usable, with the economic losses that this entails.

Finally, the devices developed so far are mainly mechanical devices, which are not capable of transmitting information on the fruit size in real time to the farmer, so that the farmer cannot use it to his or her advantage.

In fact, when using these devices and if the size of the fruit is to be known, it is necessary to move and look at it on the device itself, something that is tremendously uncomfortable if a large number of these devices have been placed in the different trees.

DESCRIPTION OF THE INVENTION

The device object of the present invention enables the problems raised in the background of the invention to be solved.

Particularly, the fruit-on-tree sizing device is a device which, due to its structure, perfectly adapts to the contour of the fruit, from when it has a small diameter of about 20-25 millimetres, until it increases in size and the moment of the picking arrives. This structure enables the fruit size to be precisely determined, but without damaging the delicate outer skin, much less causing it to deform.

Moreover, as the structure of the device is light, it does not cause the fruit to fall, even under adverse weather conditions, rain or wind, as the added weight is very low. Furthermore, the device comprises a protection compartment inside of which the necessary electronics are located, so that it is protected against water, dust, or any other external element. In fact, the device is very compact and does not require maintenance.

Lastly, the device has the important advantage that it has communication means that enable the data on the size of the fruit to be known and transmitted to an external device at all times. Moreover, the reception of the data obtained by at least 3000 or 4000 devices can be coordinated at the same time. In this way, tremendously useful information on the condition of the fruit can be obtained in real time, which can be used for decision-making.

Specifically, the fruit-on-tree sizing device comprises a lower annular disc, which has an inner compartment and a guide around its perimeter, capable of rotating about itself in one direction. First flexible arms with curved configuration start internally from the lower annular disc, each first flexible arm ending at an inner end, which together with the inner ends of the other first flexible arms define a lower opening intended for housing the fruit. Said inner end has one first hole.

An upper annular disc is positioned over the lower annular disc, parallel to the lower annular disc, capable of rotating about itself, in an opposite direction to that of the lower annular disc. Second flexible arms start internally from this second disc, each one of them ending at an inner end, which together with the inner ends of the other second flexible arms define an upper opening intended for housing the fruit. Said inner end has one second hole.

The upper annular disc has a first attachment element on the face facing the lower annular disc.

Both the assembly formed by the lower annular disc and the first flexible arms, and the one formed by the upper annular disc and the second flexible arms have a similar operation to that of the diaphragm of a photographic camera, so that, as the fruit grows, the first flexible arms and the second flexible arms contract, moving closer and closer to the lower annular disc or to the upper annular disc, as appropriate.

The device further comprises at least one bolt, connected to the upper annular disc, intended for moving along the guide when the upper annular disc rotates with respect to the lower annular disc, holding the lower annular disc and the upper annular disc together and enabling the movement of one with respect to the other.

The device further comprises means for connecting the arms, for connecting the first hole of a first flexible arm and the second hole of a second flexible arm being coincident.

In one embodiment, these means for connecting the arms can be contact parts, intended, in addition to connecting a first flexible arm with a second flexible arm, for keeping in contact with the fruit at all times, without moving with respect to the fruit, and they are the ones which transmit the force to the flexible arms, which entails the rotation of the annular discs, as the fruit grows. These connections are carried out through holes built at the ends of the arms (3 and 3').

Each of these contact parts adapts independently to the contour of the fruit, ensuring maximum support, regardless of how irregular the contour thereof is.

Alternatively, the means for connecting the arms may be adhesive means, so that each of the first flexible arms remains adhered to the corresponding second flexible arm thereof.

As the fruit increases the diameter thereof, the first flexible arms and the second flexible arms move closer and closer to the upper annular disc and to the lower annular disc, as appropriate. This causes the upper annular disc and the lower annular disc to be forced to rotate about themselves.

As the first flexible arms and the second flexible arms are arranged with curved configurations in opposite directions, the rotation of the upper annular disc and the lower annular disc will take place in opposite directions. By measuring the relative movement that takes place when one annular disc rotates with respect to another, it is possible to determine the growth of the fruit at all times, and therefore the size thereof, which is the data of main interest in this case.

Inside the inner compartment, there are second attachment elements, associated with the first attachment elements of the upper annular disc, and they are intended for moving through the inner compartment.

There is a reading module located inside the inner compartment, with a first reading element, associated with the second attachment elements, and a second reading element, positioned in the inner compartment. In this way, the first reading element is associated with the upper annular disc and the second reading element is associated with the lower annular disc. When one disc rotates with respect to another, the reading module is capable of measuring the relative movement of one disc with respect to another.

The first reading element can be associated reading pins connected to a plate in turn associated with the second attachment elements. These pins are located in correspondence with the second reading element and are the ones that measure the movement of the upper annular disc with respect to the lower annular disc. The second reading element can be a coded arc.

Finally, in the inner compartment there are also communication means intended for sending the measurement obtained by the reading module to an external device, as well as one or more batteries for powering the device.

In an embodiment of the invention, the device may comprise a protection disc, positioned over the inner compartment of the lower annular disc. Thereby, the electronic components positioned in the interior compartment are protected.

In this embodiment, both the first attachment element associated with the upper annular disc, and the second attachment element associated with the lower annular disc are magnets, associated by means of a magnetic force. Thereby, when the upper annular disc rotates, the magnet of the first attachment element is integrally pulled. In turn, this magnet pulls the second magnet of the second attachment element through the protection disc. This magnet of the second protection element, associated with the plate and therefore with the first reading element, moves it over the second reading element, as indicated above.

DESCRIPTION OF THE DRAWINGS

As a complement to the description provided herein, and for the purpose of helping to make the features of the invention more readily understandable, in accordance with a preferred practical exemplary embodiment thereof, said description is accompanied by a set of drawings constituting an integral part of the same, which by way of illustration and not limitation, represent the following.

PREFERRED EMBODIMENT OF THE INVENTION

An exemplary embodiment of the present invention is described below with help from FIGS. 1 to 9.

Figure 1:
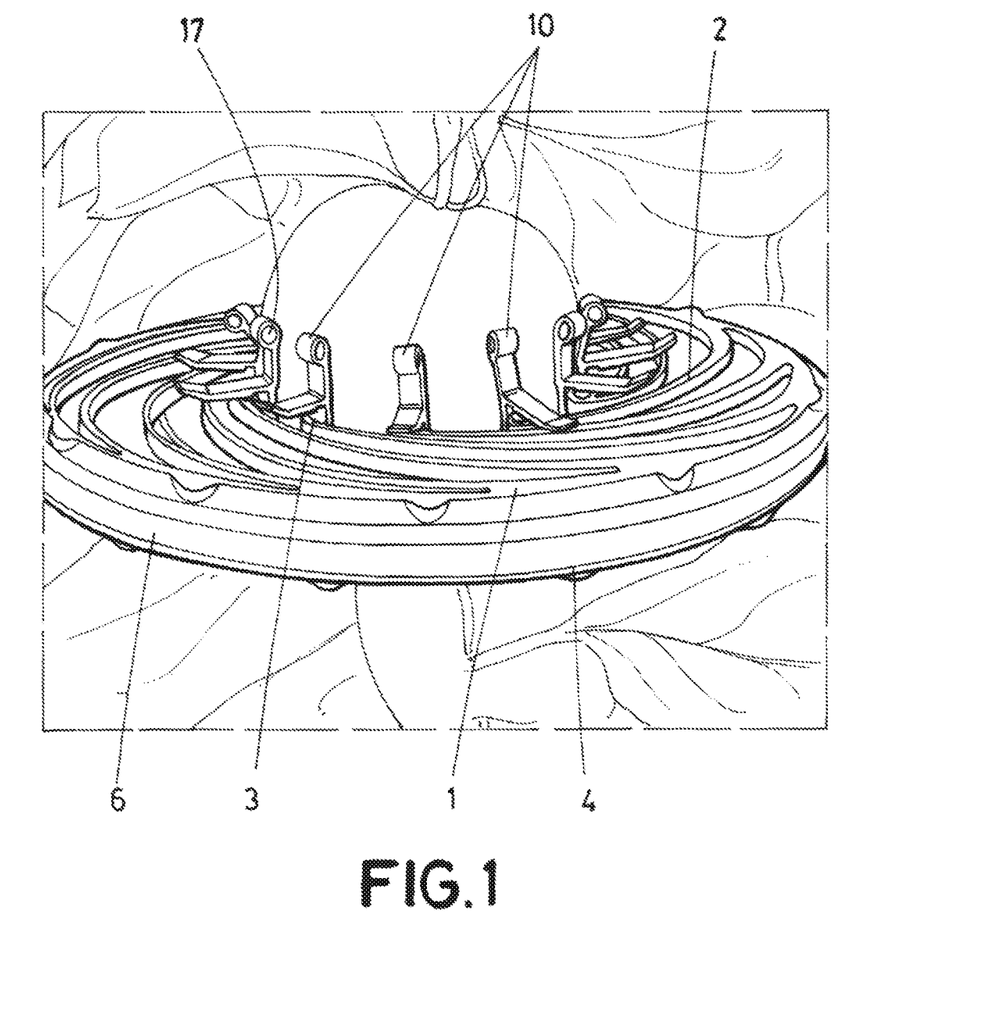
FIG. 1.—Shows a general view of an embodiment of the fruit-on-tree sizing device placed on an apple.

FIG. 1 shows the fruit-on-tree sizing device, positioned around an apple on the tree.

Figure 2:
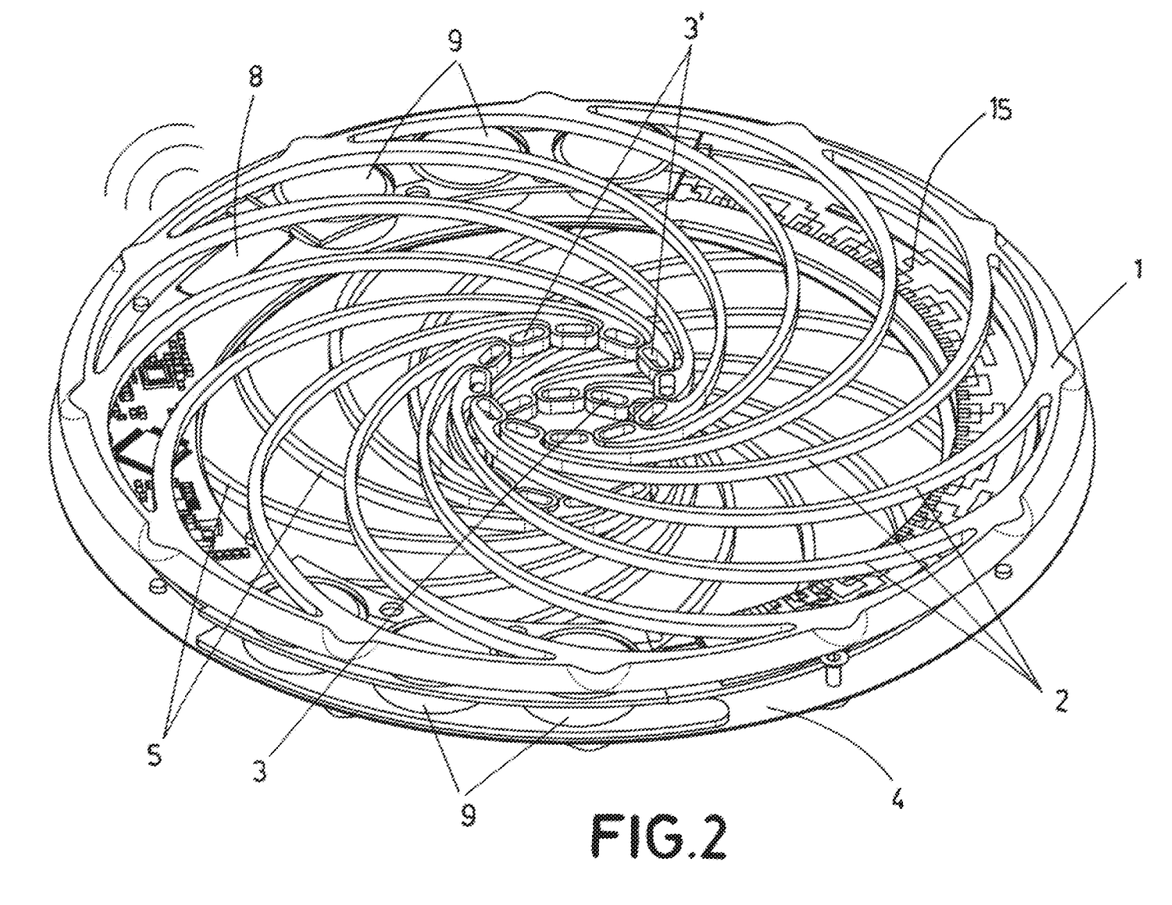
FIG. 2.—Shows a detailed view of an embodiment of the fruit-on-tree sizing device.

As can be seen in said figure, and in more detail in FIG. 2, the device comprises a lower annular disc (4) capable of rotating about itself, and which has an inner compartment (11) and a guide (12) around the perimeter thereof. The guide (12) can be seen in more detail in FIG. 6.

First flexible arms (5) with curved configuration start internally from the lower annular disc (4), which end at an inner end, which together with the inner ends of the other first flexible arms (5) define a lower opening (18) intended for housing the fruit. Said inner end has a first hole (3).

Figure 7:
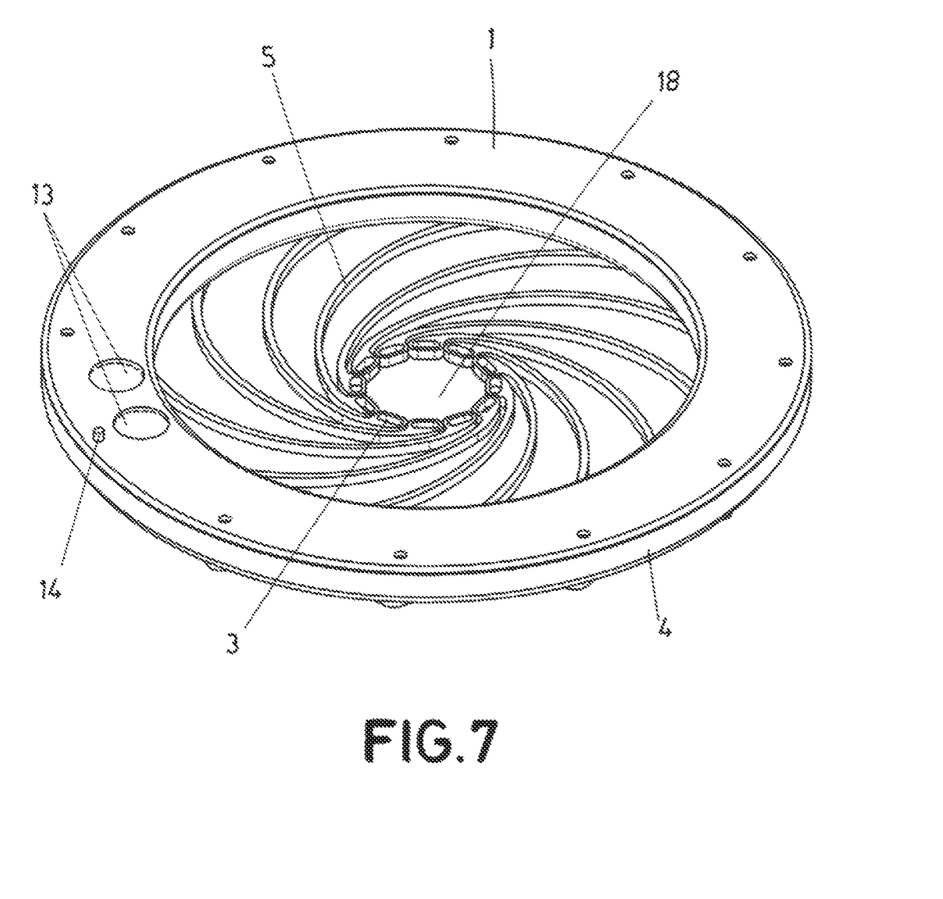
FIG. 7.—Shows a detailed view of the upper annular disc.
Figure 8:
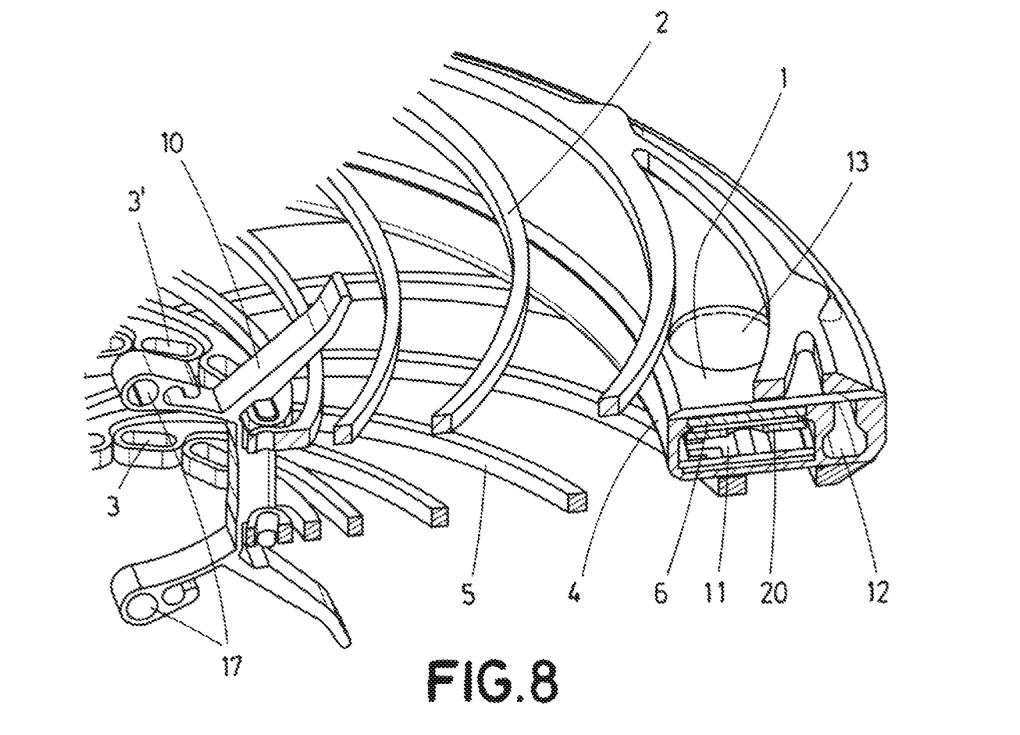
FIG. 8.—Shows a cross section of an embodiment of the device.
Figure 9:
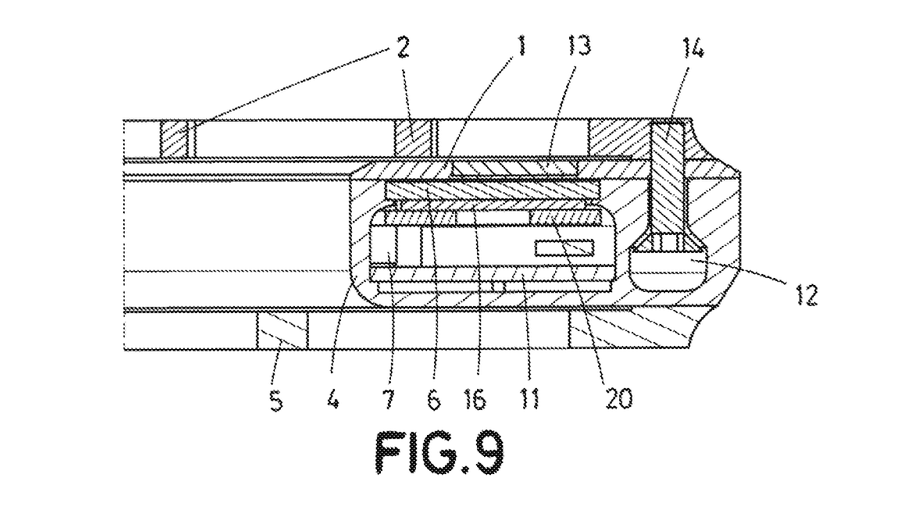
FIG. 9.—Shows a detailed view of the cross section of FIG. 8.

Furthermore, the device comprises an upper annular disc (1), shown in FIG. 7, parallel to the lower annular disc (4) and capable of rotating on itself in the opposite direction of rotation to the lower annular disc (4). Second flexible arms (2) with curved configuration start internally from the upper annular disc (1), which end at an inner end, and which together with the inner ends of the other second flexible arms (2) define an upper opening (19) intended for housing the fruit. Said inner end has a second hole (3').

The upper annular disc (1) has first magnets (13) on the face facing the lower annular disc (4).

Figure 3:
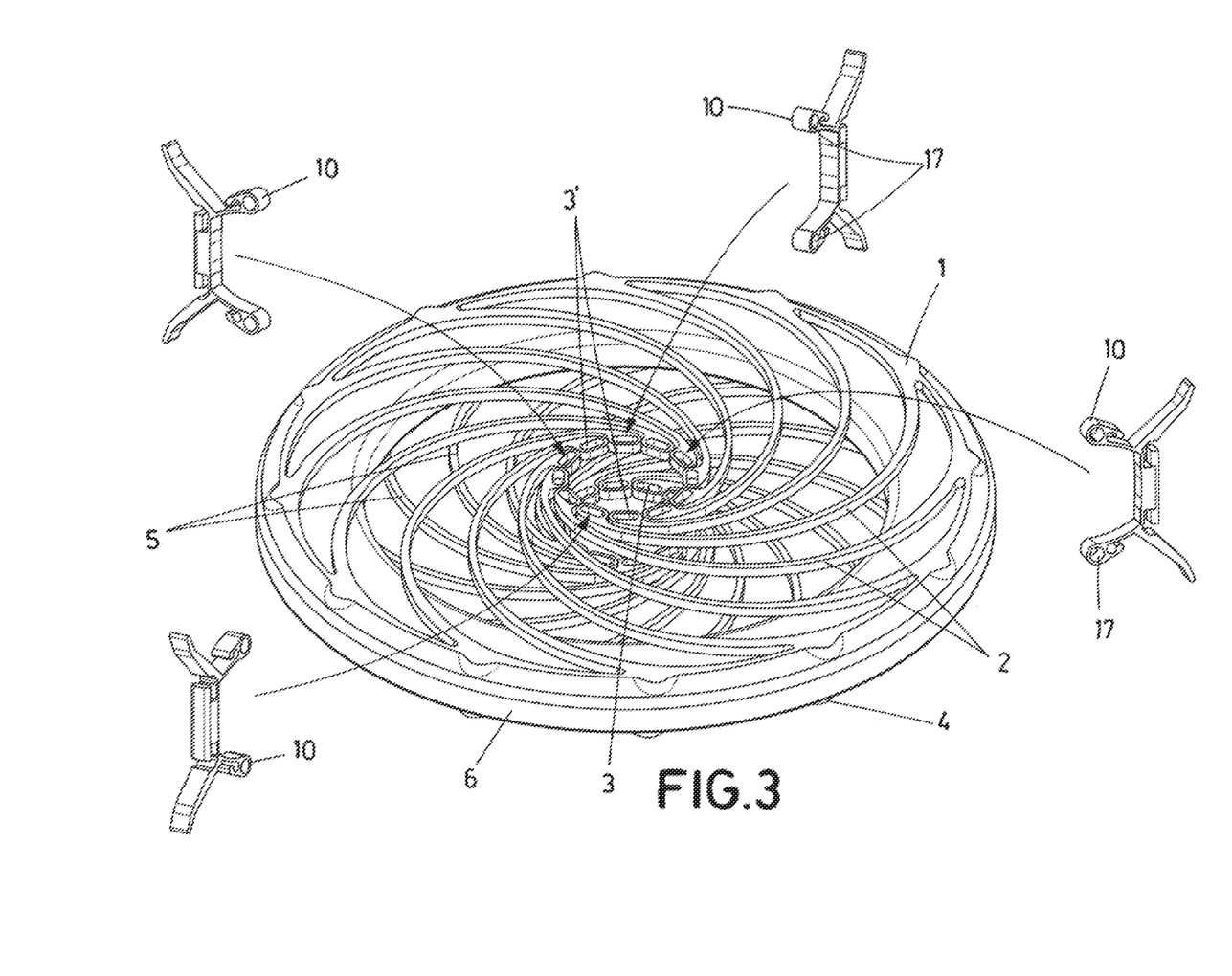
FIG. 3.—Shows a view of an embodiment of the device that has articulated ends.

As it appears in FIGS. 1 and 3, there are contact parts (10) located connected to the first holes (3) and to the second holes (3') intended for keeping in contact at all times with the fruit that is housed in the lower opening (18) and the upper opening (19). The contact parts (10) have certain mobility with respect to the first flexible arms (5) and the second flexible arms (2), being able to individually adapt to the contour of the fruit, thereby preventing them from damaging the delicate skin thereof.

The device further comprises at least one bolt (14), connected to the upper annular disc (1) and intended for moving along the guide (12) when the upper annular disc (1) rotates with respect to the lower annular disc (4), holding the lower annular disc (4) and the upper annular disc (1) together and enabling the movement of one with respect to the other.

Regarding the operation of the device, as the fruit size increases and the contact parts (10) keeping in contact with the surface thereof, without moving with respect to it, the first flexible arms (5) and the second flexible arms (2) move closer and closer to the upper annular disc (1) and to the lower annular disc (4) as appropriate.

Figure 4A:
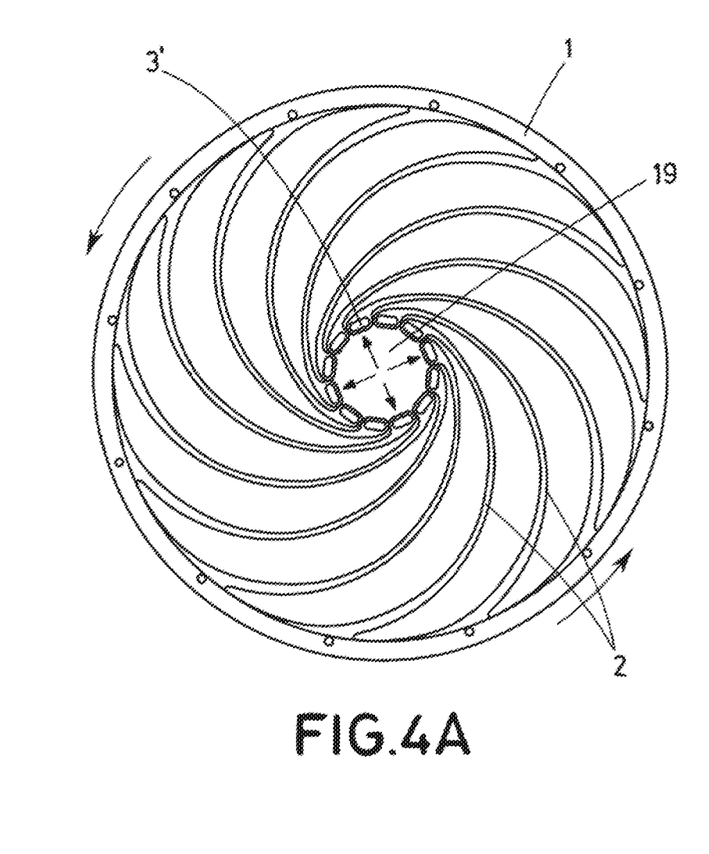
FIG. 4.—Shows a plan view of the discs and the flexible arms indicating the direction of rotation of each one of the discs as the flexible arms move when the diameter of the fruit increases.
Figure 4B:
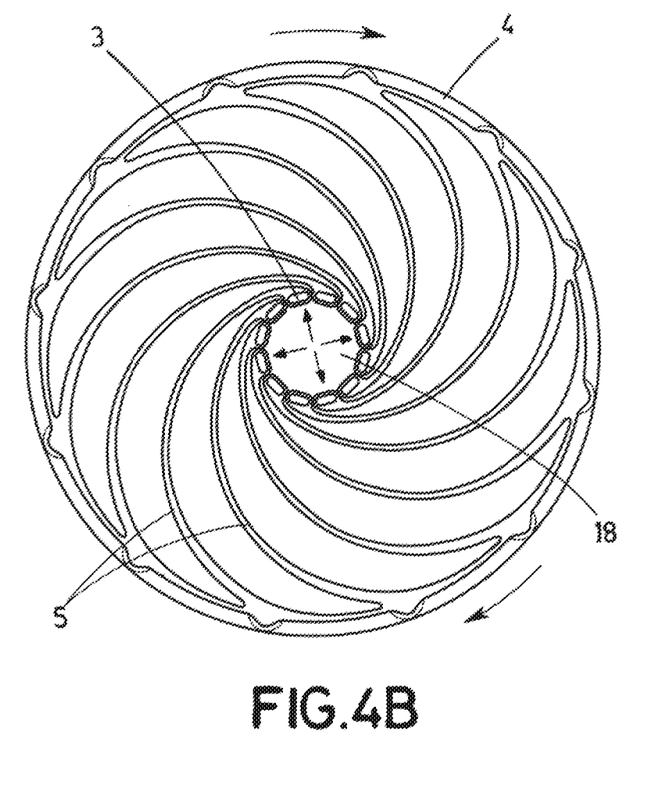

As FIG. 4 schematically represents, the first flexible arms (5) and the second flexible arms (2) behave in a similar way to a diaphragm, and since the contact parts (10) cannot move with respect to the fruit, the movement is transferred to the upper annular disc (1) and to the lower annular disc (4), forcing them to rotate about themselves. As the first flexible arms (5) and the second flexible arms (2) are positioned in opposite directions, each one of the annular discs rotates about itself in an opposite direction, one clockwise and the other counter clockwise.

In order to quantify this relative movement of the upper annular disc (1) with respect to the lower annular disc (4), the device comprises elements that are positioned in the inner compartment (11) and that are protected by means of a protection disc (6) positioned over the inner compartment (11), intended for protecting these elements against external damage, such as that caused by rain or dust.

Figure 5:
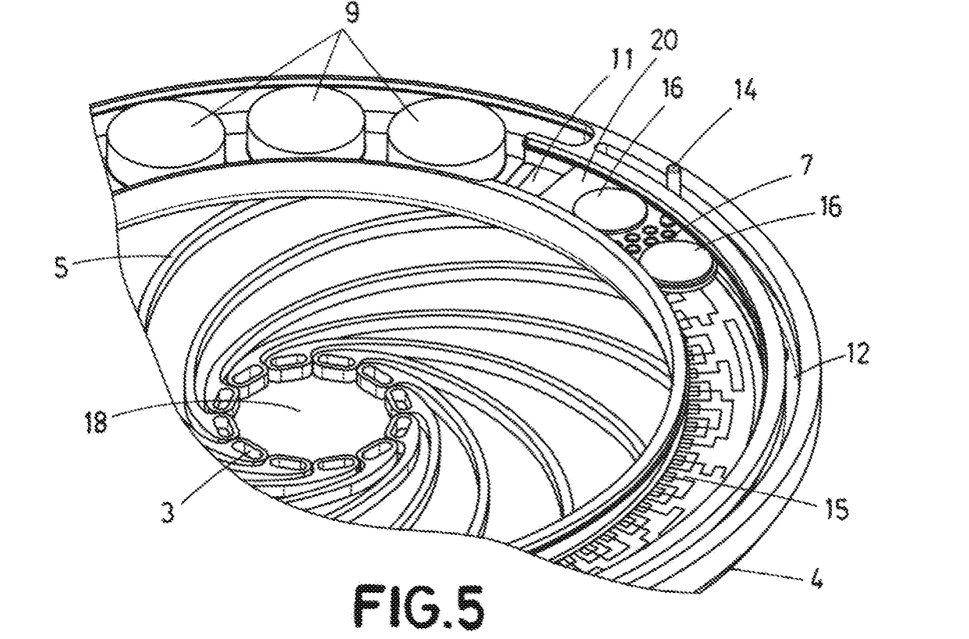
FIG. 5.—Shows a detailed view of the reading module of the device.
Figure 6:
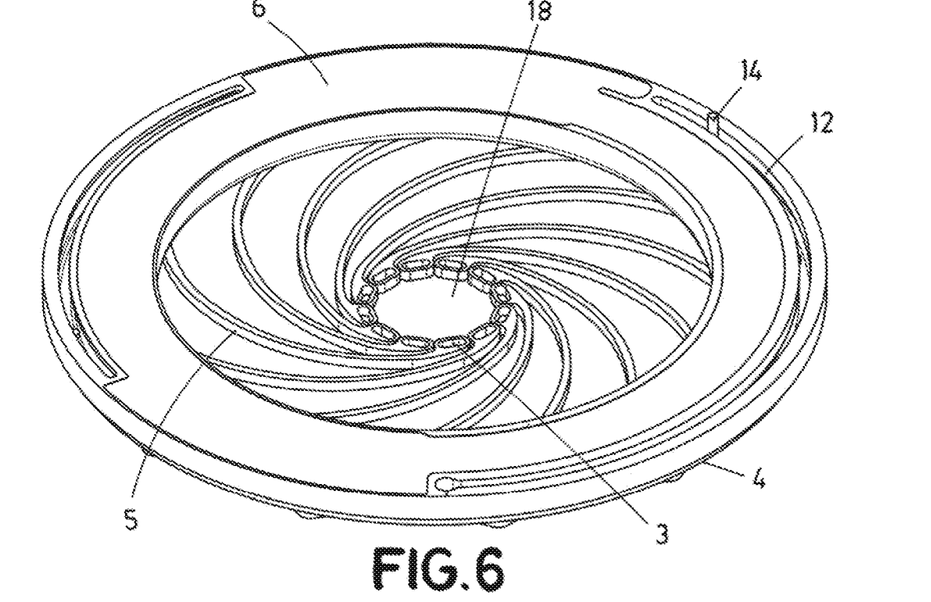
FIG. 6.—Shows a detailed view of the lower annular disc guide.

The first of these elements is a coded arc (15), which can be seen in FIG. 5, located in the inner compartment (11). Furthermore, second magnets (16) mounted on a plate (20), associated with the first magnets (13) by means of a magnetic force, the plate (20) being intended for moving through the inner compartment (11), over the coded arc (15).

Associated with the plate (20) are reading pins (7), located in correspondence with the coded arc (15) which measure the movement of the upper annular disc (1) with respect to the lower annular disc (4), following an encoder type scheme. All the above elements are shown in detail in FIGS. 8 and 9.

To be able to transmit this measurement, the device comprises communication means (8), also located in the inner compartment (11). These communication means (8) have a radio frequency antenna, intended for transmitting said data to an external device.

Finally, in order to power the device, it comprises one or more batteries (9), also in the inner compartment (11). These batteries (9) can be externally charged, to facilitate the task, as well as to avoid having to break the airtightness of the inner compartment (11).

The invention claimed is:

1. A fruit-on-tree sizing device,
wherein it comprises:
a lower annular disc that has an inner compartment and a guide around its perimeter thereof, intended for rotating in one direction, first flexible arms with curved configuration,
wherein each first flexible arm starts internally from the lower annular disc and ends at an inner end, which together with the inner ends of the other first flexible arms define a lower opening intended for housing a fruit,
wherein said inner end has a first hole, an upper annular disc, parallel to the lower annular disc and intended for rotating in the opposite direction to the lower annular disc, and which comprises a first attachment element on a face facing the lower annular disc, second flexible arms with curved configuration,
wherein each second flexible arm starts internally from the upper annular disc and ends at an inner end, which together with the inner ends of the other second flexible arms define an upper opening intended for housing the fruit,
wherein said inner end has a second hole, at least one bolt, connected to the upper annular disc and intended for moving along the guide when the upper annular disc rotates with respect to the lower annular disc, holding the lower annular disc and the upper annular disc together and enabling the movement of one with respect to the other,
a plurality of connectors, each connector connected to the first hole of a first flexible arm and to the second hole of a corresponding second flexible arm, a second attachment element associated with the first attachment element,
a reading module, which has a first reading element associated with the second attachment element, and
a second reading element located in the inner compartment of the lower annular disc,
the first reading element being located in correspondence with the second reading element,
the reading module being capable of measuring the movement of the upper annular disc with respect to the lower annular disc,
a transmitter located inside the inner compartment, intended for sending the measurement obtained by the reading module to an external device,
at least one battery for powering the device, positioned inside the inner compartment.

2. The device of claim 1, wherein it further comprises a protection disc, positioned on the inner compartment of the lower annular disc, wherein the first attachment element is a first magnet and the second attachment element is a second magnet, attracted to the first magnet through the protection disc.

3. The device of claim 1, wherein the transmitter comprise a radio frequency antenna.

4. The device of claim 1, wherein the batteries are externally rechargeable.

5. The device of claim 1, wherein the second reading element is a coded arc.

6. The device of claim 1, wherein the plurality of connectors are contact parts intended for keeping in contact with the fruit that is housed in the lower opening and the upper opening.

7. The device of claim 6, wherein the contact parts comprise ends provided with holes intended for housing a rubber band for squeezing the fruit.

8. The device of claim 1, wherein the plurality of connectors further comprise adhesives.

9. The device of claim 1, wherein the first reading element are reading pins.

* * * * *